United States Patent [19]

Oppenlaender et al.

[11] 4,031,112
[45] June 21, 1977

[54] CYCLIC ACETALS

[75] Inventors: Knut Oppenlaender, Ludwigshafen; Guenter Uhl, Worms; Herbert Helfert, Frankenthal; Hans-Georg Scharpenberg, Limburgerhof; Karl Stork, Lampertheim, all of Germany

[73] Assignee: BASF Aktiengesellschaft, Ludwigshafen, Germany

[22] Filed: Feb. 17, 1976

[21] Appl. No.: 658,524

[30] Foreign Application Priority Data

Mar. 12, 1975 Germany .......................... 2510636

[52] U.S. Cl. .................................. 260/340.7; 8/62; 252/311; 260/326.5 D; 260/332.3 H; 260/332.3 P; 260/340.9
[51] Int. Cl.² ........................................ C07D 319/04
[58] Field of Search ...................... 260/340.7, 340.9

[56] References Cited

UNITED STATES PATENTS

| | | | |
|---|---|---|---|
| 2,131,998 | 10/1938 | Billig | 260/340.7 |
| 2,441,944 | 5/1948 | Remensnyder et al. | 260/340.7 |
| 3,201,420 | 8/1965 | Fuzesi et al. | 260/340.7 |
| 3,948,953 | 4/1976 | McCoy | 260/340.9 |

*Primary Examiner*—Ethel G. Love
*Attorney, Agent, or Firm*—Keil, Thompson & Shurtleff

[57] ABSTRACT

Cyclic acetals or ketals of carbonyl compounds having at least one aliphatic or aromatic radical, and polyhydric alcohols which have at least one more hydroxyl group than those required for acetalization, and which are furthermore oxyalkylated at the free hydroxyl group or groups.

3 Claims, No Drawings

CYCLIC ACETALS

The present invention relates to new cyclic acetals or ketals of the formula I

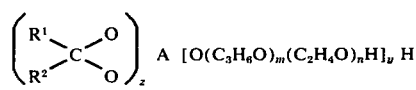   I where $R^1$ is alkyl of 1 to 20 carbon atoms, alkenyl of 2 to 20 carbon atoms, unsubstituted or substituted phenyl, or the radical of thiophene, furan or pyrrole, $R^2$ is hydrogen or has one of the meanings given for $R^1$, $R^1$ and $R^2$ being identical or different, or $R^1 + R^2$ together are an aliphatic five-membered or six-membered ring, A is a radical, free from hydroxyl groups, of a polyalcohol with $2z + y$ OH groups and of 3 to 6 carbon atoms, $z$ is 1 or 2, $y$ is 1 or 2, $m$ is from 5 to 20 and $n$ is from 10 to 100, their manufacture, and their use as industrial emulsifiers.

German Published Application No. 1,543,671 discloses cyclic acetals or ketals of glycerol, which are oxyethylated at the remaining free hydroxyl group. These products are intended to be used as detergent raw materials.

The present invention relates to acetals or ketals which are generally derived from polyalcohols of 3 to 6 carbon atoms and which, according to the invention, are first oxypropylated, and then oxyethylated, at the residual OH group or groups, i.e. the acetals or ketals are ethers of block copoylmers of propylene oxide and ethylene oxide in which the ether bridge links the polyalcohol to the poly(propylene oxide) radical.

We have also found that, in contrast to the oxyethylated products according to German Published Application No. 1,543,671, these products are excellent industrial emulsifiers.

The new products may be manufactured by a simple method which comprises acetalizing a polyalcohol of the formula II

   II with a carbonyl compound of the formula III

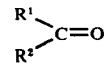   III in the molar ratio of from 2.2:1 to 2:1, or from 1.1:1 to 1:1, and subsequently oxyalkylating the acetal or ketal formed successively with $y \cdot m$ moles of propylene oxide and $y \cdot n$ moles of ethylene oxide, $R^1$, $R^2$, A, $z$, $y$, $m$ and $n$ having the above meanings.

Starting materials for the manufacture of the compounds according to the invention are aldehydes or ketones or their mixtures, as defined by formula III. In principle, it is possible to use any aldehyde or ketone falling under the above definition, provided they are free from substituents which could undergo objectionable side reactions under the conditions of the acetalization and subsequent oxyalkylation. Preferred aldehydes where $R^1$ is an aliphatic radical are those of 5 to 20 carbon atoms which conform to the above definition, and above all compounds such as caproaldehyde, heptaldehyde, octaldehyde, enanthaldehyde, lauroylaldehyde, myristylaldehyde, stearylaldehyde, oleylaldehyde, oxoaldehydes of 9 to 11 carbon atoms, oxoaldehydes of 13, 15, 16 and 18 carbon atoms and the corresponding aldehydes obtained from alcohols from the Ziegler reaction and from alcohols obtained from cracked olefins. Of course, the known lower aldehydes, starting from formaldehyde and acetaldehyde up to the butyraldehydes, can also be subjected to the reaction.

According to the above definition, aromatic aldehydes which can be used are those where $R^1$ in the molecule is substituted or unsubstituted phenyl or the radical of thiophene, furan or pyrrole; above all, benzaldehyde, o-, m- and p-nitrobenzaldehyde, salicylaldehyde, p-dimethylaminobenzaldehyde, o-, m- and p-chlorobenzaldehyde and -bromobenzaldehyde, furfuraldehyde, thiophenaldehyde and pyrrolylaldehyde may be mentioned.

Particularly preferred aldehydes are oxoaldehydes of 9 to 11 carbon atoms, oxo-aldehydes of 15 to 18 carbon atoms, benzaldehyde, p-dimethylaminobenzaldehyde and furfuraldehyde.

Ketones which can be used for the manufacture of the compounds according to the invention also includes all those which conform to the above definition, provided the reaction can take place without side reactions; acetone, methyl ethyl ketone, 2-pentanone, 2-hexanone, cyclohexanone, sym-undecanone and benzophenone are of particular interest. Mixed ketones and aliphatic-aromatic ketones, e.g. acetophenone, propiophenone and the like, should also be mentioned in this context.

The other starting materials are polyalcohols of the formula II. These may have straight chains or be branched, but after acetalization they must have one or two free OH groups in accordance with the above definition.

Examples which conform to formula II are straight-chain compounds, e.g. glycerol, $CH_2OH-CHOH-CHOHCH_2OH$, pentitols and hexitols, above all sorbitol, and also methylglycerol and ethylglycerol. If, e.g., sorbitol is employed, double acetalization is possible, i.e. two pairs of hydroxyl groups react with the carbonyl compounds, to form two six-membered rings ($z = 2$, $y = 2$).

In the case of polyhydric alcohols, five-membered or six-membered rings can be formed, a six-membered ring being somewhat favored energetically.

Of the branched-chain polyhydric alcohols, trimethylolpropane and pentaerythritol should be mentioned above all.

The reaction of the carbonyl compounds with the polyhydric alcohols is carried out in accordance with conventional methods of organic chemistry. The polyhydric alcohols and carbonyl compounds are mixed in the molar ratio of from 2.2:1 to 2:1, or from 1.1:1 to 1:1, in the presence of from 0.1 to 2 percent by weight (based on the reaction mixture) of acid catalysts, e.g. sulfuric acid, phosphoric acid or phosphorous acid, and are condensed at from 90° to 200° C, preferably at from 110° to 160° C, whilst removing the water of reaction by distillation.

The oxyalkylation is carried out in two stages in accordance with conventional methods, preferably with alkaline catalysis.

In this reaction, the acetal or ketal is first mixed with the catalyst (from 0.5 to 2 percent by weight, based on acetal or ketal) and from 5 to 20, preferably from 8 to 15, moles of propylene oxide (per free OH group) are then forced in and reacted in a closed system at from 110° to 140° C and from 2 to 10 bars pressure. Thereafter, from 10 to 100 moles, preferably from 15 to 50 moles, of ethylene oxide are forced in and allowed to react under the above conditions.

Catalysts which may be used are those conventionally employed for oxyalkylations, above all alkaline catalysts, e.g. $NaOH$, $NaOCH_3$, $NaOC_2H_5$, trimethylamine, triethylamine, triethanolamine or triisopropanolamine. Acids such as $BF_3$-etherate also act as catalysts but their use is less advisable in relation to the starting materials which can be used according to the invention.

The products obtained can be characterized by data such as the acid number, OH number, viscosity or cloud point.

The products are excellent industrial emulsifiers for a great variety of applications.

Important applications include the manufacture of dispersions and of print pastes based on such dispersions. Normal dispersions are mostly obtained by emulsion copolymerization of, e.g., butadiene and styrene, acrylic acid and acrylic acid esters, etc., as starting monomers; for the manufacture of print pastes, the dispersions as a rule also contain comonomer units which carry reactive groups, e.g. N-methylolacrylamide.

Such systems contain from about 1 to 15 percent by weight, based on the sum of the solid constituents, of the emulsifiers. The method of carrying out the emulsion copolymerization is known to those skilled in the art and requires no further illustration.

The Examples which follow illustrate the manufacture and use of the new emulsifiers; parts are by weight.

EXAMPLES

General instructions for Examples 1 to 7.

$a$ moles of carbonyl compound and $b$ moles of trimethylolpropane are mixed and 0.2 mole percent of 85 percent strength phosphoric acid is added. The condensation is then carried out for 5 hours at from 110° to 125° C, whilst stirring the mixture and at the same time removing the water by distillation. Finally, the volatile constituents are removed at 160° C and 30 mbars.

1% of sodium methylate is added to the product.

$c$ moles of propylene oxide and $d$ moles of ethylene oxide are forced in successively at 4 bars and 120° C.

Products of the formula $$\begin{array}{c} R^1 \\ R^2 \end{array}\!\!>\!\!C\!\!<\!\!\begin{array}{c} O-CH_2 \\ O-CH_2 \end{array}\!\!>\!\!C\!\!<\!\!\begin{array}{c} C_2H_5 \\ CH_2-[PO]_m[EO]_n\,H \end{array}$$

where $R^1$ and $R^2$ are defined as in formula I, are obtained. They are shown in the Table which follows:

| Ex. | Carbonyl compound | a | b | m | n | c | d | OH number |
|---|---|---|---|---|---|---|---|---|
| 1 | Oxo-aldehyde of 9 carbon atoms | 11 | 10 | 10 | 30 | 100 | 300 | 54.4 |
| 2 | Oxo-aldehyde of 9 carbon atoms | 11 | 10 | 10 | 40 | 100 | 400 | 53.8 |
| 3 | Benzaldehyde | 11 | 10 | 10 | 15 | 100 | 50 | 47.5 |
| 4 | Benzophenone | 11 | 10 | 10 | 30 | 100 | 300 | 54.5 |
| 5 | Cyclohexanone | 11 | 10 | 10 | 30 | 100 | 300 | 36.0 |
| 6 | Furfuraldehyde | 11 | 10 | 10 | 30 | 100 | 300 | 46.5 |
| 7 | o-Chloro-benzaldehyde | 11 | 10 | 10 | 22 | 100 | 220 | 52.5 |

EXAMPLE 8

$$C_6H_5-CH\!\!<\!\!\begin{array}{c}O-CH_2\\O-CH_2\end{array}\!\!>\!\!CHO[PO]_{10}[EO]_{30}\,H$$

11 Moles of benzaldehyde and 10 moles of glycerol are mixed and 0.2% of 85 percent strength phosphoric acid is added. The condensation is carried out for 5 hours at from 110° to 125° C whilst stirring, and distilling off the water through a descending condenser. Finally, all volatile constituents are removed at 160° C and 20 mm Hg.

1% of Na methylate is added to the product. 100 moles of propylene oxide and 300 moles of ethylene oxide are forced in at 3 atmospheres gauge and 120° C (OH number of the product = 50.5).

EXAMPLE 9

$$H\,EO_{30}\,PO_{10}OCH_2-CH-CH-CH-CH-CH_2-O\,PO_{10}EO_{30}H$$

(with phenyl-CH acetal bridges)

22 Moles of benzaldehyde and 10 moles of sorbitol are mixed and 0.2% of 85 percent strength phosphoric acid is added. The condensation is carried out for 5 hours at from 110° to 125° C whilst stirring and distilling off the water through a descending condenser. Finally, all volatile constituents are removed at 160° C and 20 mm Hg. 1% of Na methylate is added to the product. 200 moles of propylene oxide and 600 moles of ethylene oxide are forced in at 3 atmospheres gauge and 120° C (OH number of the product = 98.5)

EXAMPLE 10

The following are mixed in a pressure kettle, whilst stirring (= charge I): 50.00 parts of monomer consisting of 59% of butadiene, 40% of styrene and 1% of acrylic acid, followed by 1.15 parts of sodium laurylsulfate, 1.5 parts of emulsifier according to Example 3, 0.5 part of tert.-dodecylmercaptan and 28.65 parts of desalinated water.

In a further vessel, 0.4 part of ammonium persulfate is dissolved in 4.6 parts of desalinated water (= charge II).

20.0 parts of desalinated water, 0.1 part of sodium lauryl-sulfate and 0.1 part of ammonium persulfate are introduced into the polymerization kettle.

The charges I and II are run in over 6 hours at 75° C and polymerization is then continued for 2 hours.

A stable latex having a solids content of from about 48 to 50% is obtained.

EXAMPLE 11

10 Parts of emulsifier according to Example 4 are dissolved in 190 parts of water. 800 parts of gasoline (boiling range 140° – 200° C) are emulsified in this solution, whilst stirring at high speed.

A very viscous stable emulsion is obtained.

870 Parts of this emulsion are taken and the following are added successively thereto: 70 parts of a 40 percent strength aqueous copolymer dispersion of 70% of butadiene, 25% of styrene and 5% of N-methylolmethacrylamide, 10 parts of a 50 percent strength solution of urea, 10 parts of a hexamethylolmelamine hexamethyl ether, 20 parts of a 26 percent strength aqueous paste of a phthalocyanine pigment and 20 parts of a 50 percent strength solution of ammonium thiocyanate.

A stable print paste which processes well is obtained.

If a terry fabric is printed with this paste in the conventional manner by flat screen printing, and is dried and then fixed with hot air at 140° C for 5 minutes, a soft brilliant print with good fastness properties is obtained.

COMPARATIVE EXPERIMENTS

Compounds: reaction product of an oxo-aldehyde of 9 carbon atoms + trimethylolpropane.

The abbreviations EO = ethylene oxide and PO = propylene oxide will be used in this and all subsequent experiments.

|  |  | Cloud point |
|---|---|---|
| Comparison c) | with 40 EO | 76° C |
| Example 1 a) | with 10 PO . 30 EO | 64° C |
| Example 2 b) | with 10 PO . 40 EO | 62° C |

The following highly viscous emulsions were prepared using these compounds: from 5 to 20 parts of the compounds described are dissolved in from 195 to 180 parts of water. 10 parts of ammonium sulfate are dissolved thereon. 750 parts of gasoline (boiling range from 140° to 200° C) are then emulsified in the mixture at from 5,000 to 6,000 rpm. 40 parts of a formulation of copper phthalocyanine blue (C.I. Pigment Blue 15 No. 74,160), composed of 40% of pigment, 11.5% of isononylphenol reacted with 20 moles of EO, and 48.5% of water, are added to the preceding, highly viscous, emulsion, making a total of 1,000 parts.

The colored thickener emulsion thus prepared is stirred with a high speed stirrer at 6,000 rpm. The more stable an emulsion is, the longer it withstands exposure to shear forces, which is coupled with a rise in temperature. The products according to the invention, containing PO and terminal EO, behave significantly better than those which only contain ethylene oxide. The initial temperature is 23° C.

| g/kg of emulsion |  | 5 | 10 | 15 | 20 |
|---|---|---|---|---|---|
| Time | 40 EO | 2″ | 2″ | 2″ | 3″ |
|  | 10 PO 30 EO | 3″ | 20″ | 2′ | 5′ |
|  | 10 PO 40 EO | 1′ | 3′ | 4′ | 6′ |
| Temperature ° C | 40 EO | 24 | 24 | 24 | 24 |
|  | 10 PO 30 EO | 24 | 24 | 36 | 41.5 |
|  | 10 PO 40 EO | 24.5 | 32 | 36 | 43 |

Criteria in this test are:

1. The addition of weak electrolytes, e.g. ammonium sulfate, which have an adverse influence on the action of the emulsifiers.
2. The effect on the surface of the emulsion droplets and of the pigment particles.

If an adduct of the acetal with EO only is prepared, the emulsions prepared therefrom are significantly less stable.

Comparison

Starting material: Acetal from o-chlorobenzaldehyde and trimethylolpropane

|  |  | Cloud point |  |
|---|---|---|---|
| a) with 32 EO |  | 83° C | (Comparison) |
| b) with 10 PO and 22 EO |  | 53° C | (Example 7) |

| g/kg of emulsion |  | 5 | 10 | 15 | 20 |
|---|---|---|---|---|---|
| Time | 32 EO | 1′ | 1′ | 2′ | 1.5′ |
|  | 10 PO 22 EO | 5′ | 15′ | 10′ | 12′ |
| Temperature ° C | 32 EO | 23.5 | 23.5 | 29 | 24 |
|  | 10 PO 32 EO | 35 | 51 | 45 | 66.5 |

The emulsions containing the acetal which has been reacted with EO only are significantly less stable. Phase separation occurs in a relatively short time.

Comparison

Starting material: acetal from furfuraldehyde and trimethoylolpropane.

|  |  | Cloud Point |
|---|---|---|
| Comparison a) | with 40 EO | 72° C |
| Example 6 b) | with 10 PO and 30 EO | 55° C |

| g/kg of emulsion |  | 5 | 10 | 15 | 20 |
|---|---|---|---|---|---|
| Time | 40 EO | — | — | — | 20″ |
|  | 10 PO 30 EO | 2′ | 3′ | 10′ | 30′ |
| Temperature ° C | 40 EO | — | — | — | 23 |
|  | 10 PO 30 EO | 26 | 29.5 | 47 | 73.5 |

The acetal with 40 EO gives completely unstable emulsions, in which phase separation occurs almost instantaneously.

Determination of the Cloud Point

A solution of 90 parts of water, 5 parts of crystalline diammonium phosphate and 5 parts of the substance to be tested, making a total of 100 parts, was used to determine the cloud point.

Stable emulsions were prepared by emulsifying solvents in aqueous emulsifier solutions which have been prepared beforehand.

The amount of emulsifier employed is in each case 5%, based on the emulsion. Stable emulsions are obtained.

| Emulsifier according to Example | Cloud 1 | 2 | 3 | 4 | 5 | 6 | 7 | 8 | 9 |
|---|---|---|---|---|---|---|---|---|---|
| 1 | 62° C | 5 | — | — | — | — | — | — | — | — |
| 2 | 63° C | — | 5 | — | — | — | — | — | — | — |
| 3 | 46° C | — | — | 5 | — | — | — | — | — | — |
| 4 | 56° C | — | — | — | 5 | — | — | — | — | — |
| 5 | 53° C | — | — | — | — | 5 | — | — | — | — |
| 6 | 55° C | — | — | — | — | — | 5 | — | — | — |
| 7 | 57° C | — | — | — | — | — | — | 5 | — | — |
| 8 | 64° C | — | — | — | — | — | — | — | 5 | — |
| 9 | 47° C | — | — | — | — | — | — | — | — | 5 |
| Water | | 195 | 195 | 195 | 195 | 195 | 195 | 195 | 195 | 195 |
| Polypropylene oxide (molecular weight 2,000) | | 800 | — | — | — | — | — | — | — | — |
| Gasoline (boiling range 140–200° C) | | — | 800 | — | — | — | — | — | — | — |
| Stearic acid i-decyl ester | | — | — | 800 | — | — | — | — | — | — |
| Castor oil | | — | — | — | 800 | — | — | — | — | — |
| Cyclohexanone | | — | — | — | — | 800 | — | — | — | — |
| White oil (W 118) | | — | — | — | — | — | 800 | — | — | — |
| Di-2-ethylhexyl phthalate | | — | — | — | — | — | — | 800 | — | — |
| Heptane | | — | — | — | — | — | — | — | 800 | — |
| Toluene | | — | — | — | — | — | — | — | — | 800 |
| Viscosity in poise | | 50 | 75 | 280 | 55 | 70 | 65 | 69 | 85 | 39 |

We claim:

1. Cyclic acetals or ketals of the formula I

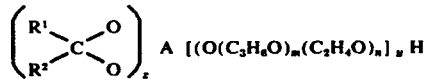  A [(O($C_3H_6O$)$_m$($C_2H_4O$)$_n$]$_y$ H    I where $R^1$ is alkyl of 1 to 20 carbon atoms, alkenyl of 2 to 20 carbon atoms, phenyl, p-nitrophenyl, hydroxyphenyl, p-dimethylaminophenyl, o-, m-, or p-chlorophenyl o-bromophenyl, $R^2$ is hydrogen or has one of the meanings defined for $R^1$, said meaning being identical to or different from $R^1$, or $R^1$ and $R^2$ together are an aliphatic five-membered or six-membered ring, A is a radical, free from hydroxyl groups, of a polyalcohol with $2z + y$ OH groups and of 3 to 6 carbon atoms, z is 1 or 2, y is 1 or 2, m is from 5 to 20 and n is from 10 to 100.

2. Cyclic acetals of the formula I as claimed in claim 1, in which $R^1$ is alkyl of 3 to 20 carbon atoms, $R^2$ is hydrogen and A is the hydroxyl-free radical of glycerol, n-butanetetrol, sorbitol, methylglycerol, ethylglycerol, trimethylolpropane or pentaerythritol.

3. Cyclic ketals of the formula I as claimed in claim 1, in which $R^1$ and $R^2$ are identical or different and each is methyl, ethyl, n-butyl, n-pentyl or phenyl, or $R^1$ and $R^2$ together are an aliphatic six-membered ring.

* * * * *